US00PP21875P2

(12) United States Plant Patent
van Herck

(10) Patent No.: US PP21,875 P2
(45) Date of Patent: Apr. 19, 2011

(54) ***HIBISCUS* PLANT NAMED 'OAK RED'**

(50) Latin Name: *Hibiscus hybrida*
Varietal Denomination: Oak Red

(75) Inventor: Guido van Herck, Herenthout (BE)

(73) Assignee: De Zonnebloem Breeding B.V., De Kwakel (NL)

( * ) Notice: Subject to any disclaimer, the term of this patent is extended or adjusted under 35 U.S.C. 154(b) by 0 days.

(21) Appl. No.: 12/590,022

(22) Filed: Oct. 30, 2009

(51) Int. Cl.
*A01H 5/00* (2006.01)

(52) U.S. Cl. ..... Plt./257

(58) Field of Classification Search ..... Plt./257
See application file for complete search history.

*Primary Examiner* — Susan B McCormick Ewoldt
(74) *Attorney, Agent, or Firm* — C. A. Whealy

(57) ABSTRACT

A new and distinct cultivar of *Hibiscus* plant named 'Oak Red', characterized by its upright, somewhat, outwardly spreading and dense and bushy plant habit; dark green-colored oakleaf-shaped leaves; freely flowering habit; large red-colored flowers; and good flower longevity.

2 Drawing Sheets

Botanical designation: *Hibiscus hybrida.*
Cultivar denomination: 'OAK RED'.

BACKGROUND OF THE INVENTION

The present invention relates to a new and distinct cultivar of *Hibiscus* plant, botanically known as *Hibiscus hybrida,* and hereinafter referred to by the name 'Oak Red'.

The new *Hibiscus* plant is a product of a planned breeding program conducted by the Inventor in Herenthout, Belgium. The objective of the breeding program is to create new compact *Hibiscus* plants with attractive and large flowers.

The new *Hibiscus* plant originated from a cross-pollination in August, 2005 in Herenthout, Belgium of an unnamed proprietary seedling selection of *Hibiscus hybrida,* not patented, as the female, or seed, parent with an unnamed proprietary seedling selection of *Hibiscus coccineus* as the male, or pollen, parent. The new *Hibiscus* plant was discovered and selected by the Inventor as a flowering plant within the progeny of the stated cross-pollination in a controlled greenhouse environment in Herenthout, Belgium in July, 2006.

Asexual reproduction of the new *Hibiscus* plant by vegetative terminal cuttings in a controlled greenhouse environment in Herenthout, Belgium since August, 2006, has shown that the unique features of this new *Hibiscus* plant are stable and reproduced true to type in successive generations.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oak Red'. These characteristics in combination distinguish 'Oak Red' as a new and distinct cultivar of *Hibiscus:*

1. Upright, somewhat, outwardly spreading and dense and bushy plant habit.
2. Dark green-colored oakleaf-shaped leaves.
3. Freely flowering habit.

4. Large red-colored flowers.
5. Good flower longevity.

Plants of the new *Hibiscus* can be compared to plants of the parent selections. Plants of the new *Hibiscus* differ primarily from plants of the parent selections in flower size and color.

Plants of the new *Hibiscus* can be compared to plants of the *Hibiscus moscheutos* 'Mauvelous', not patented. Plants of the new *Hibiscus* differ from plants of 'Mauvelous' in the following characteristics:

1. Plants of the new *Hibiscus* are more compact, uniform and outwardly spreading than plants of 'Mauvelous'.
2. Plants of the new *Hibiscus* have oakleaf-shaped leaves whereas plants of 'Mauvelous' have oval-shaped leaves.
3. Flowers of plants of the new *Hibiscus* and 'Mauvelous' differ in color as plants of 'Mauvelous' have pink-colored flowers.

BRIEF DESCRIPTION OF THE PHOTOGRAPHS

The accompanying colored photographs illustrate the overall appearance of the new *Hibiscus* plant, showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Oak Red' grown in a container.

The photograph on the second sheet is a close-up view of a typical flower of 'Oak Red'.

DETAILED BOTANICAL DESCRIPTION

The aforementioned photographs and following observations, measurements and values describe plants grown in De Kwakel, The Netherlands in five-liter containers in a glass-covered greenhouses during the summer under conditions which closely approximate commercial *Hibiscus* production. During the production of the plants, day temperatures ranged from 18° C. to 33° C. and night temperatures ranged from 15° C. to 25° C. Plants were 16 weeks old when the photographs and the description were taken. In the description, color references are made to The Royal Horticultural Society Colour Chart, 2007 Edition, except where general terms of ordinary dictionary significance are used.

Botanical classification: *Hibiscus hybrida* 'Oak Red'.

Parentage:

*Female, or seed, parent.*—Unnamed proprietary seedling selection of *Hibiscus hybrida,* not patented.

*Male or pollen parent.*—Unnamed proprietary seedling selection of *Hibiscus coccineus,* not patented.

Propagation:

*Type.*—By vegetative terminal cuttings.

*Time to initiate roots, summer.*—About seven days at temperatures of 22° C.

*Time to initiate roots, winter.*—About ten days at temperatures of 22° C.

*Time to produce a rooted young plant, summer.*—About three weeks at temperatures of 21° C.

*Time to produce a rooted young plant, winter.*—About five weeks at temperatures of 20° C.

*Root description.*—Medium in thickness, fibrous; white to light brown in color.

*Rooting habit.*—Freely branching; dense.

Plant description:

*Plant and growth habit.*—Upright, somewhat outwardly spreading and dense and bushy plant habit; moderately vigorous growth habit.

*Branching habit.*—Freely branching, usually about eight lateral branches develop; pinching enhances lateral branch development.

*Plant height.*—About 46.4 cm.

*Plant diameter* (*area of spread*).—About 68 cm.

Lateral branch description:

*Length.*—About 25.3 cm.

*Diameter.*—About 7 mm.

*Internode length.*—About 1.7 cm.

*Strength.*—Moderately strong.

*Texture.*—Smooth, waxy.

*Color.*—Initially, close to 177A; with development, close to 144A with waxy layer between 147C and 148C.

Foliage description:

*Arrangement.*—Alternate, single; numerous; symmetrical.

*Length.*—About 15.4 cm.

*Width.*—About 13.7 cm.

*Shape.*—Ovate to broadly ovate; oak-leaf shaped.

*Apex.*—Apiculate.

*Base.*—Cordate.

*Margin.*—Palmately-lobed; bluntly serrate and slightly undulate.

*Texture, upper and lower surfaces.*—Smooth, glabrous.

*Luster, upper surface.*—Glossy.

*Luster, lower surface.*—Matte.

*Venation pattern.*—Pinnate.

*Color.*—Developing leaves, upper surface: Close to 143A. Developing leaves, lower surface: Close to 143B. Fully expanded leaves, upper surface: Close to N137A; venation, between 144A and 146A. Fully expanded leaves, lower surface: Close to 147B; venation, close to 144B.

*Petiole.*—Length: About 8.4 cm. Diameter: About 4 mm. Texture, upper and lower surfaces: Smooth, glabrous. Color, upper and lower surfaces: Close to 144A; towards the base, tinged with close to 176B to 176C.

Flower description:

*Flower arrangement.*—Large rotate flowers arranged singly at terminal leaf axils or in terminal clusters; uniform, continuous and freely flowering habit with numerous flower buds and/or open flowers per plant at one time; flowers face mostly upright to slightly outwardly.

*Fragrance.*—None detected.

*Flower longevity.*—Good flower longevity, flowers last for about four days; flowers not persistent.

*Natural flowering season.*—Plants flower from late summer until the autumn in The Netherlands.

*Flower diameter.*—About 20.1 cm.

*Flower length* (*height*).—About 6.5 cm.

*Flower bud.*—Rate of opening: Flowers buds open in about five days. Length: About 3.9 cm. Diameter: About 3.4 cm. Shape: Broadly ovate. Color: Between 143A and 144A.

*Petals.*—Arrangement: Corolla consists of five petals that are fused at base; petals imbricate. Length: About 10.3 cm. Width: About 11.5 cm. Shape: Orbicular to flabellate. Apex: Rounded. Base: Attenuate. Margin: Entire. Texture: Smooth, glabrous. Color: When opening, upper surface: Close to 53A. When opening, lower surface: Close to 46A. Fully opened, upper surface: Close to 53B; towards the base, close to 46A to 46B; color becoming closer to 53B to 53C with development. Fully opened, lower surface: Close to 53B.

*Sepals.*—Appearance: Five sepals fused into a tubular star-shaped calyx. Length: About 4 cm. Width: About 2.4 cm. Shape: Ovate. Apex: Acute. Margin: Entire. Texture, upper and lower surfaces: Smooth, glabrous. Color, upper surface: Close to 144A; towards the base, close to 145B. Color, lower surface: Close to 144A.

*Peduncles.*—Length: About 3.3 cm. Diameter: About 2.5 mm. Angle: About 40° from the lateral branch axis. Strength: Moderately strong. Texture: Smooth, glabrous. Color: Close to 144A.

*Reproductive organs.*—Androecium: Stamen number: Numerous, about 100. Filament length: About 6 mm. Filament color: Close to 53B. Anther shape: Orbicular. Anther length: About 2 mm. Anther color: Close to 180A to 180B. Amount of pollen: Moderate to abundant. Pollen color: Close to 161A. Gynoecium: Pistil length: About 6.3 cm. Style length: About 6 cm. Style texture: Smooth, waxy. Style color: Close to 53C to 53D; towards the base, close to 54B to 54C. Stigma appearance: Five-parted, rounded. Stigma color: Close to 53A. Ovary color: Close to 150C.

*Seeds/fruits.*—Seed and fruit development have not been observed.

Temperature tolerance: Plants of the new *Hibiscus* have been observed to have tolerate temperatures from about −20° C. to about 40° C.

Pathogen/pest resistance: Plants of the new *Hibiscus* have not been observed to be resistant to pathogens and pests common to *Hibiscus*.

It is claimed:

1. A new and distinct *Hibiscus* plant named 'Oak Red' as illustrated and described.

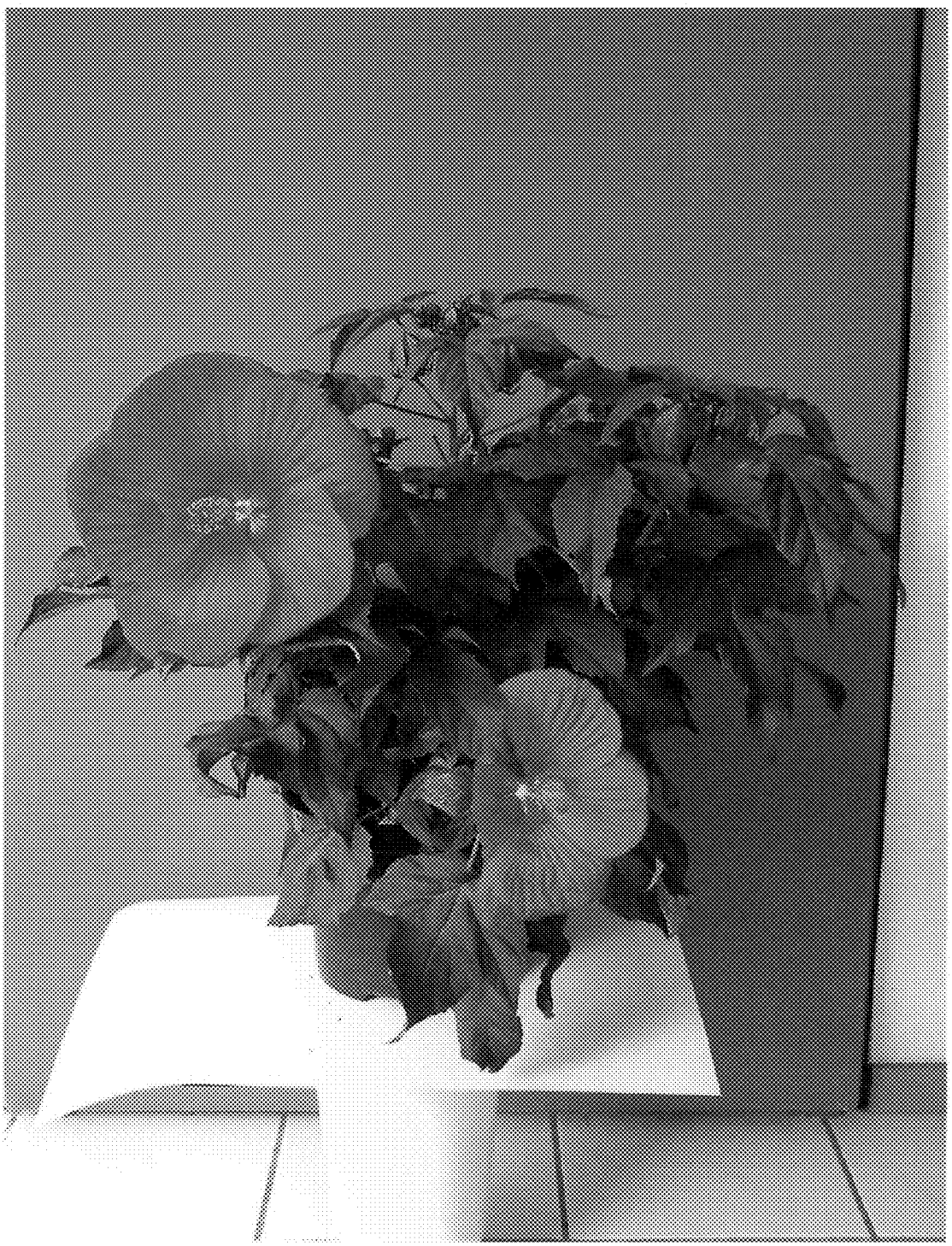

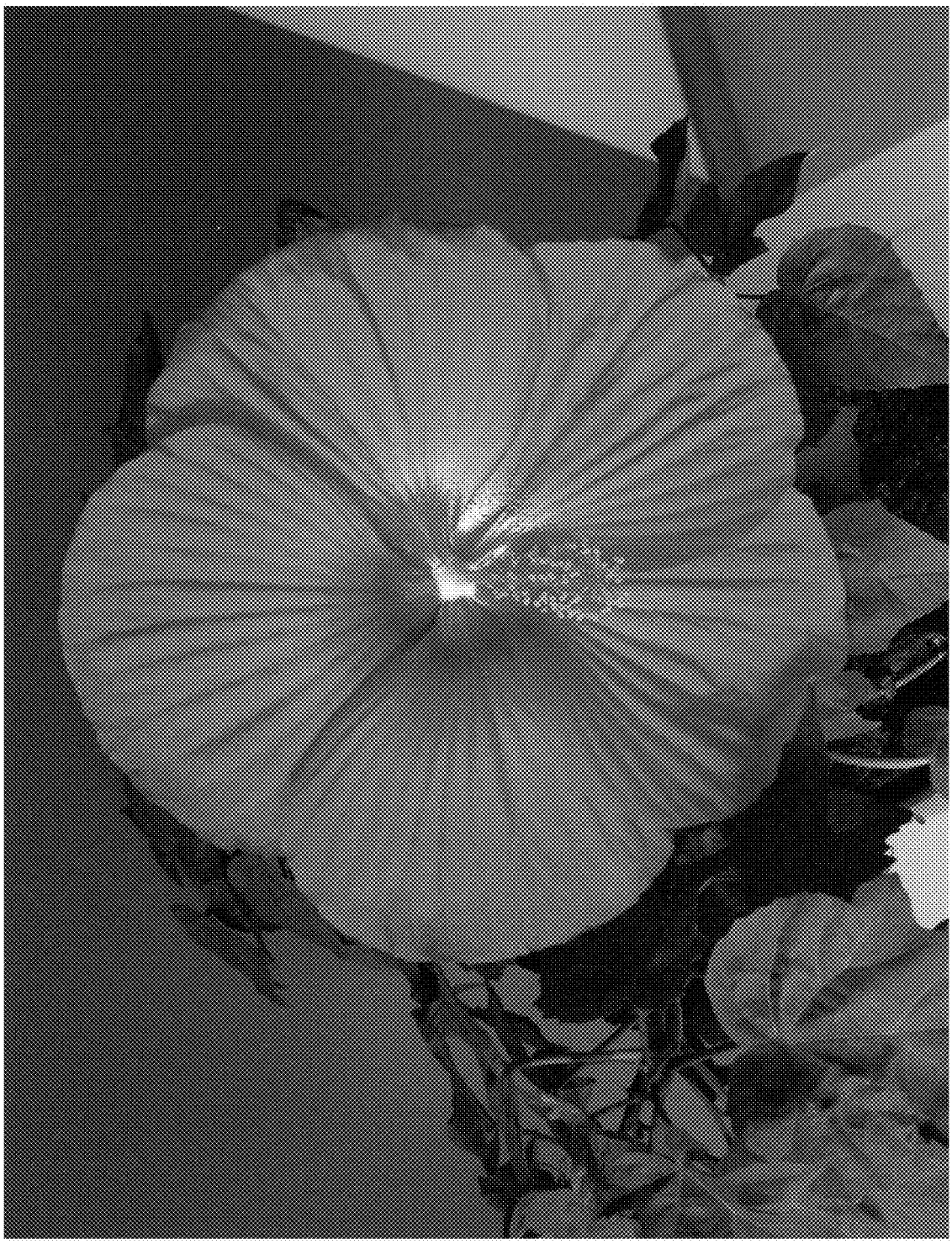

* * * * *